(12) United States Patent
Wersland et al.

(10) Patent No.: US 11,600,383 B2
(45) Date of Patent: Mar. 7, 2023

(54) NETWORKED THEFT PREVENTION AND MUTLI-USER SYNCHRONIZATION SYSTEM AND METHOD FOR PERCUSSIVE MASSAGE DEVICE

(71) Applicant: Therabody, Inc., Los Angeles, CA (US)

(72) Inventors: Jason Wersland, Manhattan Beach, CA (US); Benjamin Nazarian, Beverly Hills, CA (US); Jaime Sanchez Solana, Los Angeles, CA (US); Eduardo Merino, Beverly Hills, CA (US); Gregory L. Chambers, Beverly Hills, CA (US); Daniel Delshad, Beverly Hills, CA (US); Nick Trosko, Beverly Hills, CA (US)

(73) Assignee: Therabody, Inc., Los Angeles, CA (US)

( * ) Notice: Subject to any disclaimer, the term of this patent is extended or adjusted under 35 U.S.C. 154(b) by 0 days.

(21) Appl. No.: 17/066,015

(22) Filed: Oct. 8, 2020

(65) Prior Publication Data

US 2021/0104318 A1 Apr. 8, 2021

Related U.S. Application Data

(60) Provisional application No. 62/912,392, filed on Oct. 8, 2019.

(51) Int. Cl.
| | |
|---|---|
| *G16H 40/63* | (2018.01) |
| *G16H 20/30* | (2018.01) |
| *G06Q 20/40* | (2012.01) |

(52) U.S. Cl.
CPC ........... *G16H 40/63* (2018.01); *G06Q 20/401* (2013.01); *G16H 20/30* (2018.01)

(58) Field of Classification Search
CPC ........... G06Q 50/22–24; G06Q 20/401; G16H 40/63; G16H 20/30
See application file for complete search history.

(56) References Cited

U.S. PATENT DOCUMENTS

| | | | |
|---|---|---|---|
| 2006/0074455 A1* | 4/2006 | Strandberg | A61N 1/37252 607/30 |
| 2008/0185888 A1* | 8/2008 | Beall | A47C 7/727 297/217.4 |

(Continued)

FOREIGN PATENT DOCUMENTS

| | | | | |
|---|---|---|---|---|
| CN | 209154392 U | * | 7/2019 | ............... A61H 1/00 |
| WO | WO-2009102279 A1 | * | 8/2009 | ............. G06F 21/31 |

OTHER PUBLICATIONS

McFarland, M. (Oct. 30, 2018). Segway was supposed to change the world, two decades later, it just might. CNN Wire Service. (Year: 2018).*

(Continued)

*Primary Examiner* — Christopher L Gilligan
*Assistant Examiner* — Emily Huynh
(74) *Attorney, Agent, or Firm* — Sterne, Kessler, Goldstein & Fox P.L.L.C.

(57) ABSTRACT

A percussive massage device theft prevention system includes a percussive massage device, a command center configured to generate a unique activation code configured to be received by the percussive massage device, and an authentication device configured to be paired with the percussive massage device and provide the activation code to the percussive massage device. The percussive massage device is configured to be paired with the authentication device, receive the authentication code from the authentication device, and activate the percussive massage device for a specified time period.

13 Claims, 8 Drawing Sheets

(56) References Cited

U.S. PATENT DOCUMENTS

| | | |
|---|---|---|
| 2010/0176919 A1 | 7/2010 | Myers |
| 2011/0055720 A1 | 3/2011 | Potter |
| 2013/0304642 A1 | 11/2013 | Campos |
| 2014/0305747 A1 | 10/2014 | Kumar et al. |
| 2016/0045661 A1* | 2/2016 | Gray ................. G16H 10/60 604/500 |
| 2016/0127129 A1* | 5/2016 | Chee ................. G06F 3/04817 713/189 |
| 2016/0243359 A1 | 8/2016 | Sharma |
| 2016/0269486 A1 | 9/2016 | Gupta et al. |
| 2017/0216136 A1* | 8/2017 | Gordon ............. A61H 23/0263 |
| 2018/0140502 A1 | 5/2018 | Shahoian et al. |
| 2020/0090175 A1* | 3/2020 | Davis ................. H04W 4/80 |
| 2020/0261307 A1 | 8/2020 | Wersland |

OTHER PUBLICATIONS

PCT/US2020/054773 International Search Report & Written Opinion dated Jan. 12, 2021.

\* cited by examiner

NETWORKED THEFT PREVENTION AND MUTLI-USER SYNCHRONIZATION SYSTEM AND METHOD FOR PERCUSSIVE MASSAGE DEVICE

CROSS-REFERENCE TO RELATED APPLICATIONS

This application claims the benefit of U.S. Provisional Patent Application No. 62/912,392, filed on Oct. 8, 2019, the entirety of which is incorporated by reference herein.

FIELD OF THE INVENTION

The present invention relates generally to a system and method related to massage devices.

BACKGROUND OF THE INVENTION

As percussive massage devices become more prolific, gym and/or club locations are in need of percussive massage devices in connection with fitness, wellness, muscle recovery, and muscle activation. The gym and/or club locations, however, are also rightly concerned about preventing the theft of the percussive massage devices by gym or club members. In addition, it is desirable for more than one user to use percussive massage devices at, for example, the end of a scheduled gym session. Accordingly, there is a need to provide synchronization of the percussive massage devices so that the users may operate the devices for the same purposes and using the same routines.

The background description disclosed anywhere in this patent application includes information that may be useful in understanding the present invention. It is not an admission that any of the information provided herein is prior art or relevant to the presently claimed invention, or that any publication specifically or implicitly referenced is prior art.

SUMMARY OF THE PREFERRED EMBODIMENTS

In accordance with a first aspect of the present invention there is provided a percussive massage device theft prevention system includes a percussive massage device, a command center configured to generate a unique activation code configured to be received by the percussive massage device, and an authentication device configured to be paired with the percussive massage device and provide the activation code to the percussive massage device. The percussive massage device is configured to be paired with the authentication device, receive the authentication code from the authentication device, and activate the percussive massage device for a specified time period.

In a preferred embodiment, the percussive massage device may be activated for one hour. However, this is not a limitation and in other embodiments, the percussive massage device may be activated for other periods of time (e.g., any time period from 5 minutes to several hours to several days).

The percussive massage device may be configured to be in an inactive state unless activated by the activation code. In a preferred embodiment, the percussive massage device further includes a wireless communication module. The unique activation code may be a payment activation code. The percussive massage device theft prevention system may further include a payment portal configured to receive a payment authorization from the authentication device and provide the activation code to the authentication device.

The method of preventing theft of a percussive massage device may generate a unique activation code configured to be received by the percussive massage device, provide the activation code to an authentication device configured to be paired with the percussive massage device, pair the authentication device with the percussive massage device, provide the activation code to the percussive massage device from the authentication device, and activate the percussive massage device for a specified time period. Payment authorization may be received from the authentication device, and the activation code may be sent to the authentication device.

A method of preventing theft of a percussive massage device may receive a wireless signal from the percussive massage device at a remote device, determine whether the percussive massage device is on a list of cleared devices, and deactivate the percussive massage device if the percussive massage device is not on the list of cleared devices.

The percussive massage device in a deactivated mode may be unlocked if the percussive massage device receives an unlock command.

A multi-user percussive massage device system includes a first slave device configured to broadcast a current time and receive a broadcast message, a second slave device configured to receive a broadcast message, and a master device configured to receive the broadcast message from the first slave device and relay the broadcast message to the second slave device. The second slave device is configured to, upon receiving the broadcast message from the master device, send a confirmation packet to the master device. The master device is configured to receive the confirmation packet and relay the confirmation packet to the first slave device. An assumed network latency is determined based on the difference between the time the first slave device broadcast the current time and the time the confirmation packet is received by the master device, such that the first slave device and the second slave device synchronously operate.

The first slave device, the second slave device, and the master device may operate according to the Bluetooth standard.

A method of synchronously operating multiple percussive massage devices may broadcast a current time of a first slave device, receive the broadcasted current time at a master device, relay the broadcasted current time from the master device to a second slave device, return a confirmation packet from the second slave device to the master device, relay the confirmation packet from the master device to the first slave device, determine an assumed network latency based on the difference between the time the first slave device broadcast the current time and the time the confirmation packet is received by the master device, and synchronously operate the first slave device and the second slave device based on an offset determined by the assumed network latency.

An exemplary percussive massage device that can be used with the present invention is described in U.S. Patent Publication No. 2020/0261307 (the "'307 publication"), the entirety of which is incorporated by reference herein. In particular, any of the routines described in the '307 publication can be implemented in the multi-user percussive massage device system described herein.

BRIEF DESCRIPTION OF THE DRAWINGS

The invention may be more readily understood by referring to the accompanying drawings in which.

Like numerals refer to like parts throughout the several views of the drawings.

DETAILED DESCRIPTION OF THE PREFERRED EMBODIMENTS

Figure 1:
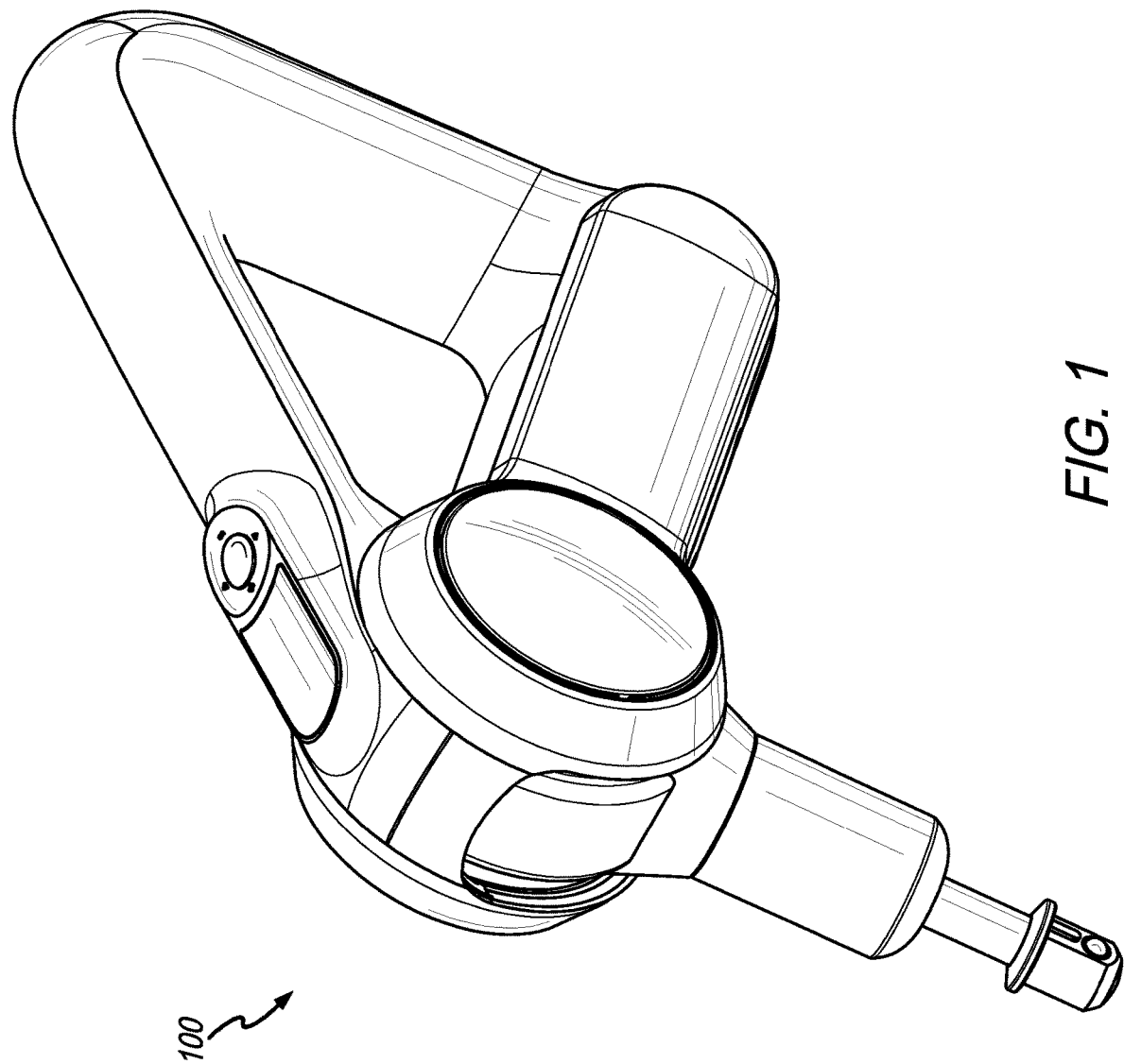
FIG. 1 is a drawing of an exemplary percussive massage device.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments. If a component is not shown in a drawing then this provides support for a negative limitation in the claims stating that that component is "not" present. However, the above statement is not limiting and in another embodiment, the missing component can be included in a claimed embodiment.

Reference in this specification to "one embodiment," "an embodiment," "a preferred embodiment" or any other phrase mentioning the word "embodiment" means that a particular feature, structure, or characteristic described in connection with the embodiment is included in at least one embodiment of the-disclosure and also means that any particular feature, structure, or characteristic described in connection with one embodiment can be included in any embodiment or can be omitted or excluded from any embodiment. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others and may be omitted from any embodiment. Furthermore, any particular feature, structure, or characteristic described herein may be optional. Similarly, various requirements are described which may be requirements for some embodiments but not other embodiments. Where appropriate any of the features discussed herein in relation to one aspect or embodiment of the invention may be applied to another aspect or embodiment of the invention. Similarly, where appropriate any of the features discussed herein in relation to one aspect or embodiment of the invention may be optional with respect to and/or omitted from that aspect or embodiment of the invention or any other aspect or embodiment of the invention discussed or disclosed herein.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present invention.

FIGS. 1-5 are directed to a system for preventing theft of a percussive massage device. In particular, FIG. 1 is a drawing of an exemplary percussive massage device 100. Many of the components and characteristics of the percussive massage device 100 are the same or similar as those discussed in the applications incorporated by reference herein.

The present invention includes a system and method for the prevention of theft. The system helps prevent percussive massage devices from being stolen and, in a preferred embodiment, uses a network approach. In a preferred embodiment, the devices 100 have Bluetooth or other connectivity capability. Accordingly, every device 100 has a Bluetooth MAC address that is the unique identifier of the device. So the device 100, when not connected to a smart device, is searching for a smart device to be able to connect to. When the device 100 connects to a smart device that includes the application (e.g., a software application or "app") installed on it, if that MAC address or that unique serial number of that device is on a "stolen or misplaced" list, then the device will be locked and cannot be used or will not turn on. Instead, the application will prompt the user to take an action, such as call customer service. For example, if a device owner reports a device as stolen, the identifying number of that device will be listed in a database. When the individual who stole the device turns the device on and it connects to the their mobile device with the app thereon (or any other mobile device), the device will lock or switch from a usable state to a non-usable state. This system is a network based theft deterrent that prevents gyms or other device owners from having to physically tether the device to prevent theft.

Figure 2:
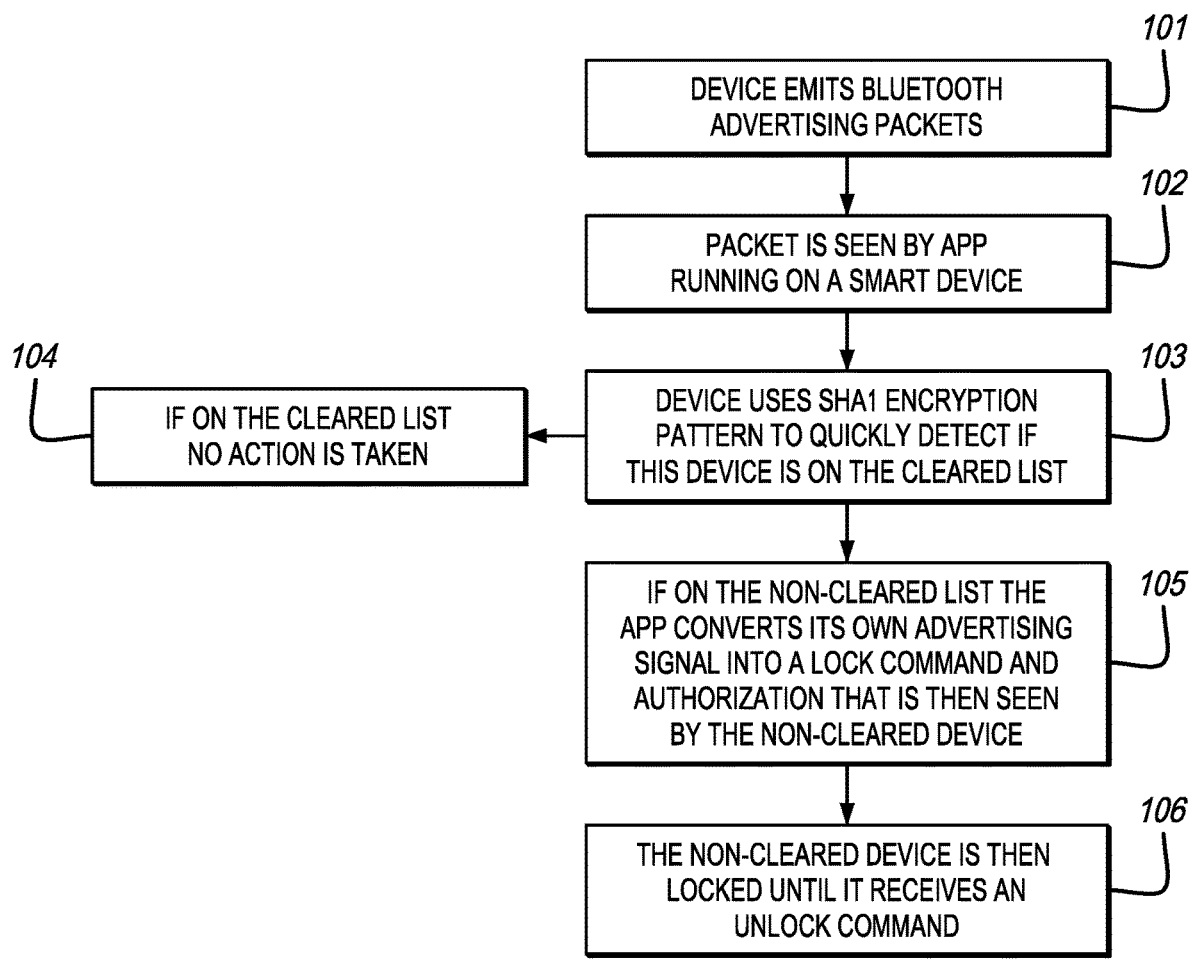
FIG. 2 is a flow chart related to a system and method for the prevention of theft for fitness, wellness, muscle recovery, and muscle activation devices.

FIG. 2 is a flow chart related to a system and method for the prevention of theft for fitness, wellness, muscle recovery, and muscle activation devices (e.g., percussive massage devices). One of ordinary skill in the art will understand that while the Bluetooth Standard is referenced in this particular embodiment, other wireless standards may be utilized without departing from the scope of the present invention.

In a preferred embodiment, as shown in FIG. 2, at Step 101 the percussive massage device 100 emits an advertising packet per the Bluetooth Standard. In this single packet is a unique identifier. At Step 102 an application running on a smart device sees this single packet. At Step 103, the application converts the unique identifier to SHA1 hash encryption (or other encryption protocol). This SHA1 encryption is then checked against a data store of devices identifiers that are "not cleared" for any number of reasons including suspected theft. At Step 104, if the device is on the cleared list, no action is taken. At Step 105, if the device is seen on the not-cleared list the application running on the smart device modifies its own Bluetooth advertising packet to include a lock code and authorization. The new advertising packet from the app running on the smart device is seen by the percussive massage device 100. At Step 106 the percussive massage device 100 locks itself until it receives the proper unlock code and authorization.

Figure 3:
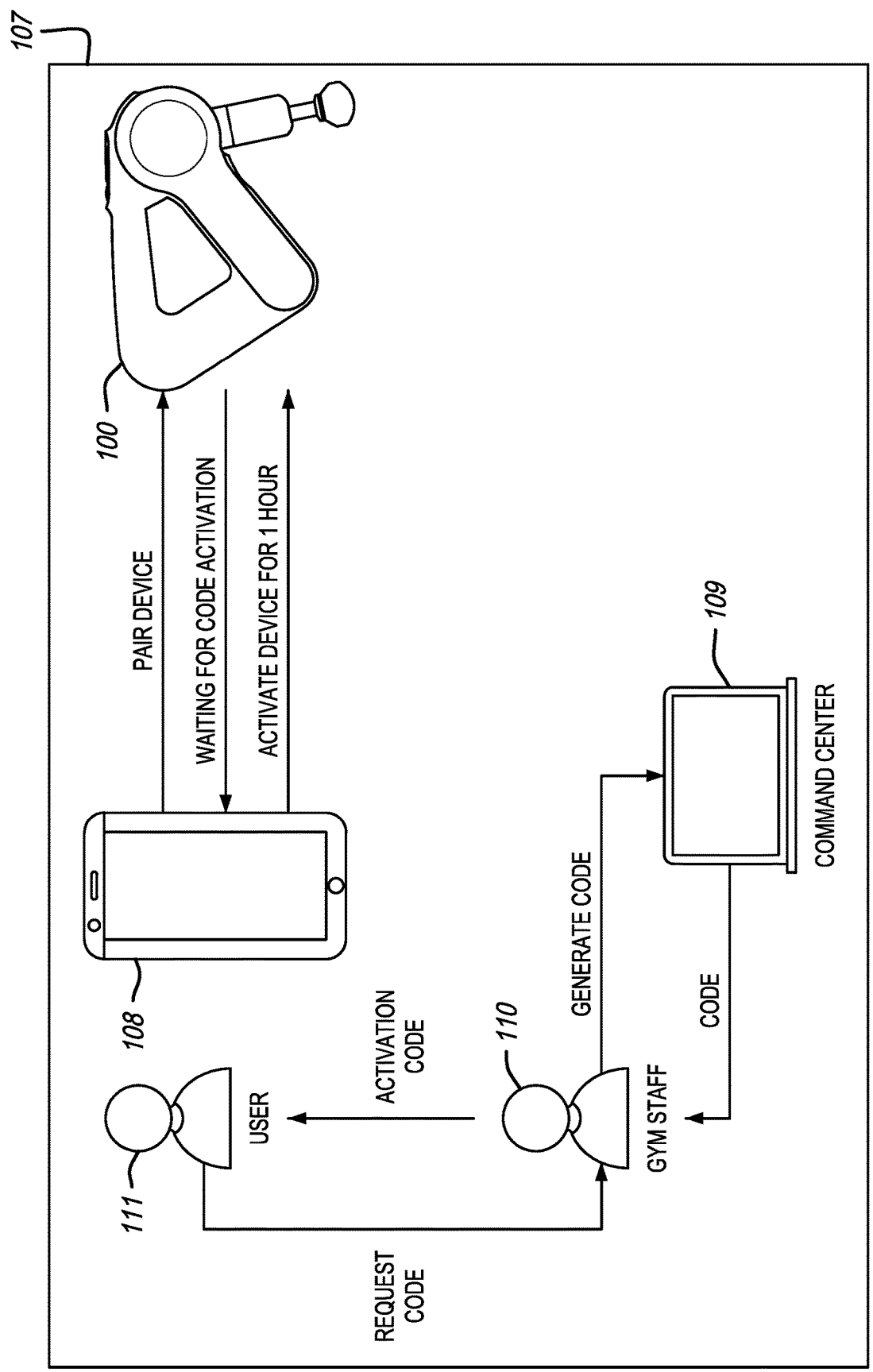
FIG. 3 is a system block diagram of percussive massage device theft prevention system in accordance with an embodiment of the present invention.

FIG. 3 is a system block diagram of percussive massage device theft prevention system 107 in accordance with an embodiment of the present invention. The system 107 includes a percussive massage device 100, a smart device 108, and a command center 109.

The device 100 is, for example, the device 100 depicted in FIG. 1 herein. The smart device 108 is, for example, a smart phone capable of executing a software application. In an embodiment, the smart device 108 is configured to pair with the device 100, wait for an activation code, and then activate the device for a specified or predetermined time period. In an embodiment, as shown in FIG. 3, the device is activated for 1 hour.

The command center 109 is configured to generate a unique activation code specified for a unique or particular percussive massage device device 100. The command center 109 may include a list of percussive massage device devices 100 for which activation codes may be generated. In FIG. 3, a gym staff member requests the command center 109 to generate a code, and the gym staff member 110 receives the unique activation code corresponding to the unique device 100. The gym staff member 110 then may provide the activation code to a user 111, who may input the activation code into the smart device 108.

In another embodiment, the user 111 may request the command center 109 to generate a code, and the user may directly receive the unique activation code. For example, the smart device 108 may be configured, upon input from the user 111 to request the code directly from the command center 109. The command center 109 may be located at the same location as the device 100 and/or the smart device 108. Alternatively, the command center 109 may be located at a remote server, e.g., a cloud-based server, and be capable of receiving requests from the smart device 108 at a remote location. One of ordinary skill in the art would understand that the user 111 cannot have access to the command center 109 without permission from the owner (e.g., gym owner) of the device 100.

In an embodiment, the user 111 initiates the process of requesting an activation code, and the device 100 will be in an inactive state until it receives a unique activation code from the smart device 108. The device 100, in an embodiment, sends a message to the smart device 108 that the device 100 is waiting for code activation. The inactive state may, in an embodiment, restrict use of the device 100. In other embodiments, the device 100 may be inoperable, set in an idle mode, or otherwise be set in a mode so that the user 111 (or others) cannot operate the device 100 for its intended purpose. In an embodiment, the device 100 will remain in an inactive state to prevent the use of the device 100 unless a unique identification code is input. Thus, if the device 100 is stolen, it would be practically useless because it would be inoperable without a unique activation code. In yet another alternative, the device 100 may be capable of receiving a manually input activation code.

Figure 4:
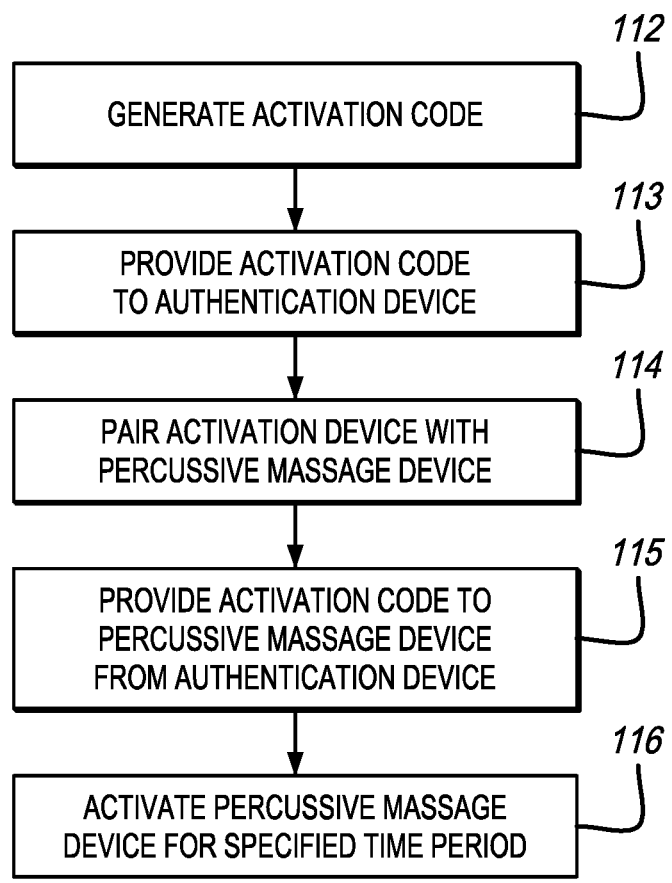
FIG. 4 is a flowchart related to a system and method of preventing theft of a percussive massage device in accordance with an embodiment of the present invention.

FIG. 4 is a flowchart related to a system and method of preventing theft of a percussive massage device in accordance with an embodiment of the present invention.

At Step 112, a unique activation code is generated. For example, a command center 109 generates the unique activation code, as described above in connection with FIG. 3.

At Step 113, the unique activation code is provided to an authentication device. For example, the authentication device is the smart device 108. The authentication device includes the capability of communicating with the device 100.

At Step 114, the authentication device is paired with the percussive massage device 100. A "pairing" of two devices is well known process suitable for a variety of wireless connectivity standards, including the BLE Standard.

At Step 115, the unique activation code is provided to the device 100 using the authentication device. At this step, the devices are already paired to establish the ability to transmit and receive data.

At Step 116, the device 100 is activated for a specified time period. For example, the device 100 is activated for 1 hour.

Figure 5:
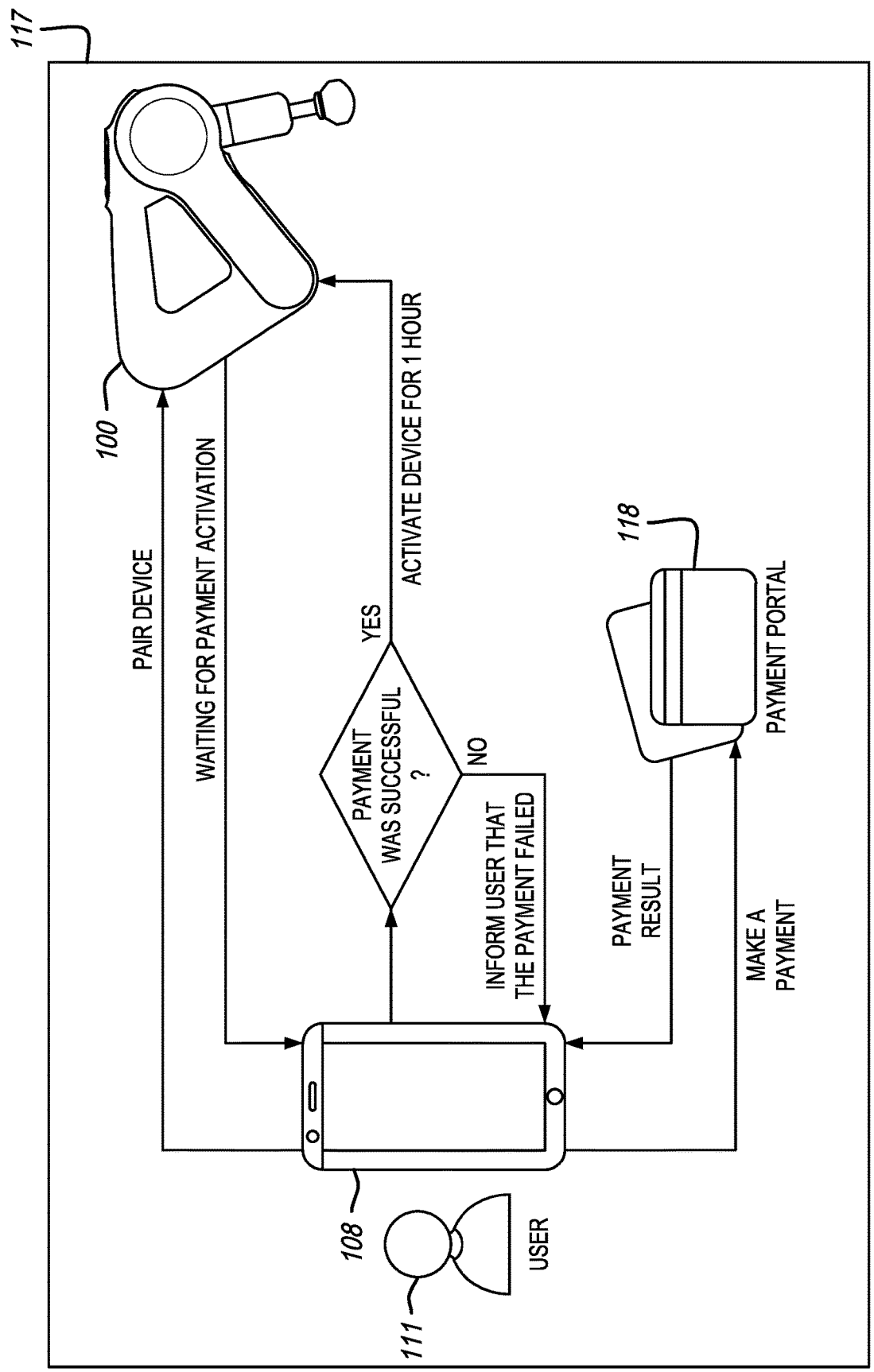
FIG. 5 is a system block diagram of percussive massage device theft prevention system in accordance with an embodiment of the present invention.

FIG. 5 is a system block diagram of percussive massage device theft prevention system 117 in accordance with an embodiment of the present invention. The system 117 includes a percussive massage device 100, a smart device 108, and a payment portal 118.

The device 100 is, for example, the device 100 depicted in FIG. 1 herein. The smart device 108 is, for example, a smart phone capable of executing a software application. In an embodiment, the smart device 108 is configured to pair with the device 100, wait for a payment activation, and then activate the device for a specified time period. In an embodiment, as shown in FIG. 5, the device is activated for 1 hour.

The payment portal 118 is configured to receive a payment from the smart device 108. For example, the user 111 initiates the payment process on the smart device 108 via a software application. The payment portal 118 then provides the smart device 108 with a payment result based on the success or failure of the payment. If the payment failed, the smart device 108 informs the user 111 that the payment failed. If the payment was successful, the smart device 108 informs the device 100 to activate for a specified time period. The payment portal 118 may include a list of devices 100 for which payment authentication may be generated. The payment portal 118 may be a payment provider.

The payment portal 118 may be located at the same location as the device 100 and/or the smart device 108. Alternatively, the payment portal 118 may be located at a remote server, e.g., a cloud-based server, and be capable of receiving requests from the smart device 108 at a remote location.

In an embodiment, the user 111 initiates the payment process, and the device 100 will be in an inactive state until it receives payment activation from the smart device 108. The device 100, in an embodiment, sends a message to the smart device 108 that the device 100 is waiting for code activation. The inactive state may, in an embodiment, restrict use of the device 100. In other embodiments, the device 100 may be inoperable, set in an idle mode, or otherwise be set in a mode so that the user 111 (or others) cannot operate the device 100 for its intended purpose. In an embodiment, the device 100 will remain in an inactive state to prevent the use of the device 100 unless it receives payment activation. Thus, if the device 100 is stolen, it would be practically useless because it would be inoperable without payment activation. In yet another alternative, the device 100 may be capable of receiving a manually input payment activation.

Figure 6:
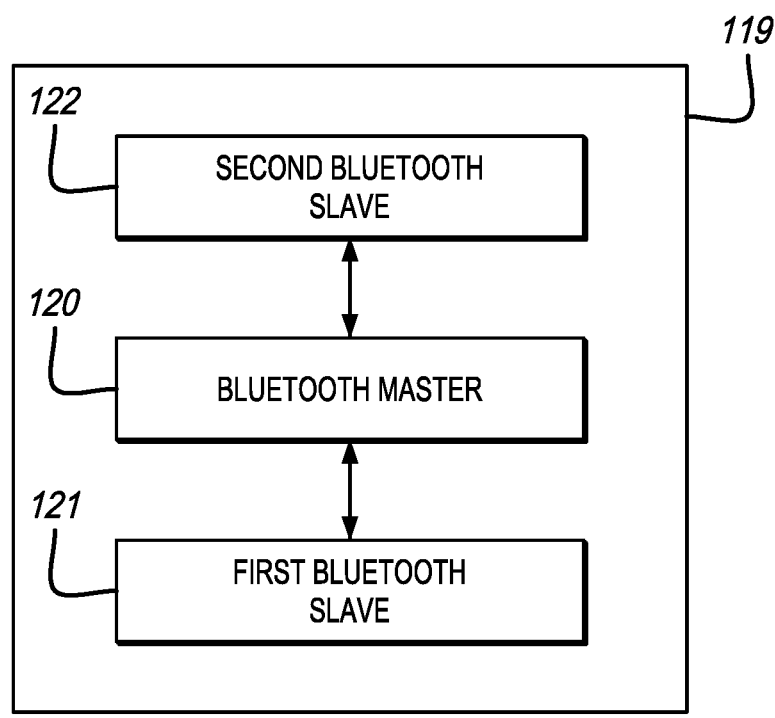
FIG. 6 is a system block diagram depicting a multi-user percussive massage device system in accordance with an embodiment of the present invention.
Figure 7:
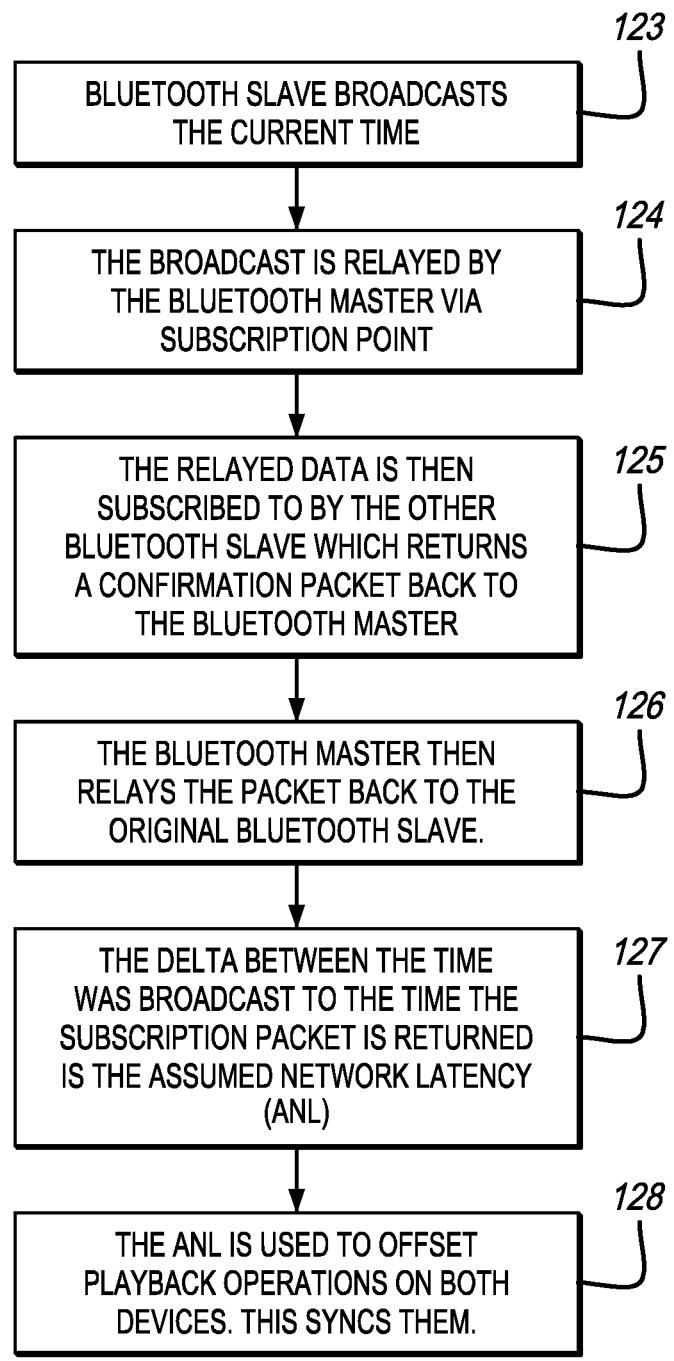
FIG. 7 shows a flowchart related to a system and method for the content and sequence synchronization for multiple devices at the same time in fitness, wellness, muscle recovery, and muscle activation setting.
Figure 8:
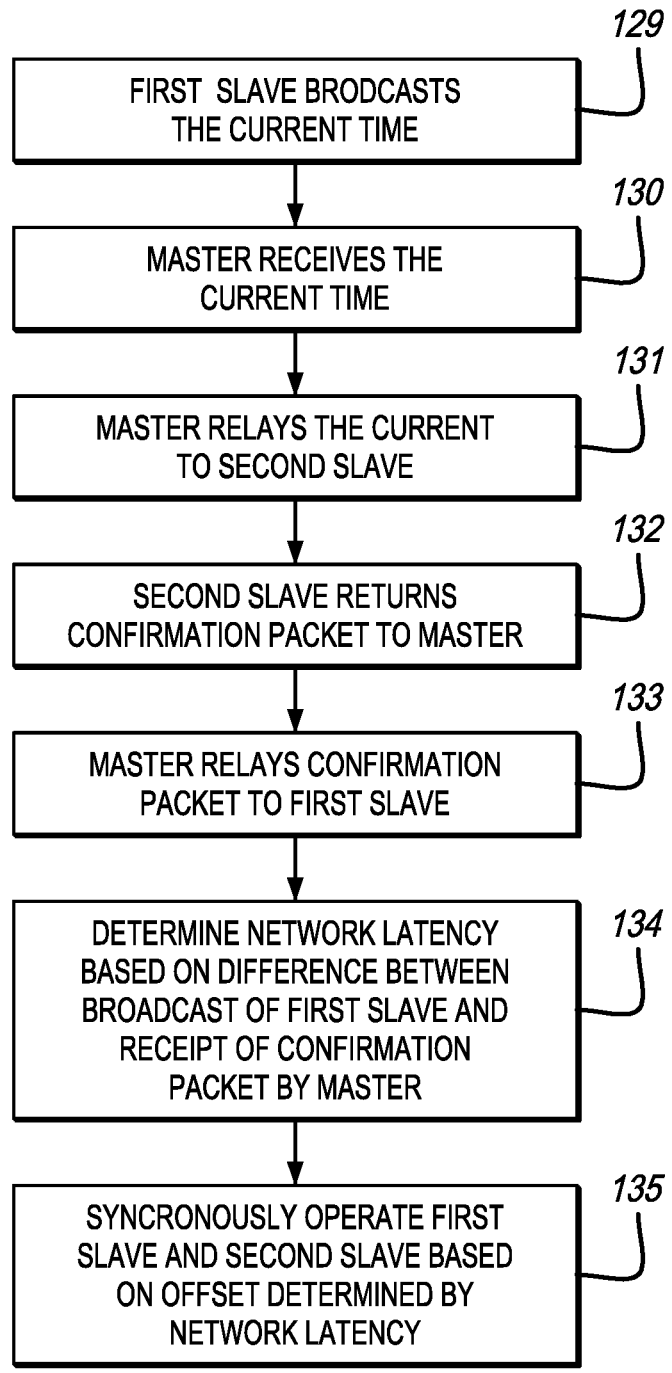
FIG. 8 is a flowchart of a method of synchronously operating multiple percussive massage devices in accordance with an embodiment of the present invention.

FIGS. 6-8 are directed to a multi-user percussive massage device system. For example, a plurality of the percussive massage devices 100 shown in FIG. 1 can be used. This system can be used, for example, so that a gym can provide classes using the device 100. In use, the class includes a plurality of users that each have one of a plurality of devices 100. When the group of devices are all synced, each device within the group will operate in synchrony. For example, the devices may turn on and off at predetermined times, may change frequency at predetermined times, may change stroke, among other actions.

The use of the device 100 shown in FIG. 1 is not a limitation and any type of percussive massage device can be used. Moreover, the use of percussive massage devices is not a limitation and other types of exercise or therapy devices can be used in the system and method described herein.

In particular, FIG. 6 is a system block diagram depicting a multi-user percussive massage device system in accordance with an embodiment of the present invention. One of ordinary skill will understand that while the Bluetooth Standard is referenced in this particular embodiment, other wireless standards may be utilized without departing from the scope of the present invention.

FIG. 6 includes a Bluetooth Low Energy (BLE) network 119 including a Bluetooth master 120, a first Bluetooth slave 121, and a second Bluetooth slave 122. One of ordinary skill in the art would understand that more than two Bluetooth slaves may be operated in accordance with the BLE standard depending on the desired application. Further, while reference is made to "master" and "slave" other references to network hierarchy or topology may be referred to within the scope of the present invention. For example, the first Bluetooth slave 121 and the second Bluetooth slave 122 are exercise devices. In an embodiment, the first Bluetooth slave 121 and the second Bluetooth slave 122 are each the device 100. In an embodiment, the master 120 is a standalone computer, laptop, or entertainment center. In an embodiment, the master 120 is located in a gym or club. In an embodiment, the master 120 is communicably coupled with an off-site database and processor, and/or application configured to provide an exercise routine to the master 120 which, in turn, provides synchronous operation of the first slave 121 and the second slave 122 according to that routine. In an embodiment, the master 120 is an exercise device. In another embodiment, the master 120 is the percussive massage device 100. One of ordinary skill in the art would understand that other arrangements of the master/slave hierarchy or topology are possible without departing from the scope of the present invention.

As one of ordinary skill in the art would understand, the BLE network 119 is a wireless personal area network (or piconet) designed to provide reduced power consumption and cost. The BLE Standard is therefore suitable for applications in which a battery-powered device 100 is utilized.

The master 120 is configured to coordinate communication throughout the piconet. The master 120 may transmit to and receive data from any slave devices within its piconet. The first slave 121 and second slave 122 are configured to transmit and receive data to the master 120.

FIG. 7 is a flowchart related to a system and method for the content and sequence synchronization for multiple devices at the same time in fitness, wellness, muscle recovery, and muscle activation setting. As described herein, Bluetooth devices operate on a master/slave relationship as per the BLE standard. This means a slave device can only be connected to one master and thus cannot be synchronized with other slave devices. The present invention broadcasts an encrypted version of the current time (synchronized from the US atomic clock) from one slave to the master and to another slave via a publisher/subscriber model. The synchronized time data point is then used as a real-time offset to a percussive massage device, such as the device 100. This process of using a time offset gives the user the impression that all the devices are operating in-sync with each other.

In a preferred embodiment, the present invention includes a system for syncing a plurality of devices so that the plurality of devices operate in synchronicity. As described above, the system can be used, for example, so that a gym can provide classes using a plurality of the devices 100.

In an embodiment, the system includes synchronization that allows all the devices to synchronize over a mesh network, such that the speed and management of the devices is done from a centralized point, which allows them to stay in sync with each other so that everyone in the class experiences the percussive massage treatment the same way at the same time.

At Step 123, the Bluetooth slave 121 broadcasts the current time. At Step 124, the broadcast is relayed by the Bluetooth master 120 via a subscription point. At Step 125, the relayed data is then subscribed to by another Bluetooth slave 122 which returns a confirmation packet back to the Bluetooth master 120. At Step 126, the Bluetooth master 120 then relays the packet back to the original Bluetooth slave 121. At Step 127, the delta between the time the time was broadcast to the time the subscription packet is returned is the assumed network latency (ANL). At Step 128, the ANL is used to offset playback operations on both devices, which syncs the slaves 121, 122. One of ordinary skill in the art would understand that more than two slaves may be utilized in a master/slave BLE network.

FIG. 8 is a flowchart of a method of synchronously operating multiple percussive massage devices in accordance with an embodiment of the present invention.

At Step 129, the first slave 121 broadcasts the current time. As described herein, the first slave 121 is capable of retrieving and broadcasting an encrypted version of the current time (synchronized from the US atomic clock). One of ordinary skill in the art would understand that other synchronizations are possible without departing from the scope of the present invention.

At Step 130, the master 120 receives the current time broadcast from the first slave 121. At Step 131, the master 120 relays the current time to the second slave 122. At Step 132, the second slave 122 returns a confirmation packet to the master 120. At Step 133, the master 120 relays the confirmation packet to the first slave 121. At Step 134, network latency is determined based on the difference between the broadcast time of the first slave 121 and the receipt time of the confirmation packet by the master 120. At Step 135, the first slave 121 and the second slave 122 are synchronously operated based on an offset determined by the network latency.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Furthermore, the synchronization system described herein can be combined with the anti-theft system discussed herein. For example, a plurality of users (e.g., first and second users) can each obtain a percussive massage device (e.g., first and second percussive massage devices) and authenticate each of the devices according to the system taught in FIGS. 2-5 so that they are activated for a predetermined period of time. The first and second users can then take the authenticated percussive massage devices (or their own personal percussive massage devices) to a designated area (e.g., a classroom) within the gym, connect to the master device and/or system (e.g., using the subject app on their phone) and then use the devices synchronously during a class. As a result, the first and second users can participate in a class or session where their percussive massage device starts and stops, changes frequency, etc. during use. The instructor in the class can instruct the users regarding various steps or changes in the routine, such as where to use the device (i.e., which body part), what grip to use (see the first, second and third handle portions in FIG. 1 and the '307 publication), what attachment to use (e.g., ball, cone, etc.). In another embodiment, the instructions can be provided via a display, such as a television, monitor, screen or the like instead of being given by the instructor.

In another embodiment, the master device can be the instructor's device. Therefore, when the instructor starts and stops the device (using a switch or button), the slave devices start and stop. Similarly, when the instructor changes the frequency on the master exercise device, the frequency changes on the first and second slave devices.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodi-ments using the singular or plural number may also include the plural or singular number re-spectively. The word "or" in reference to a list of two or more items, covers all of the following interpretations of the word: any of the items in the list, all of the items in the list, and any com-bination of the items in the list.

The above-detailed description of embodiments of the disclosure is not intended to be exhaustive or to limit the teachings to the precise form disclosed above. While specific embodiments of and ex-amples for the disclosure are described above for illustrative purposes, various equivalent mod-ifications are possible within the scope of the disclosure, as those skilled in the relevant art will recognize. Further, any specific numbers noted herein are only examples: alternative imple-mentations may employ differing values, measurements or ranges.

Although the operations of any method(s) disclosed or described herein either explicitly or implicitly are shown and described in a particular order, the order of the operations of each method may be altered so that certain operations may be performed in an inverse order or so that certain operations may be performed, at least in part, concurrently with other operations. In another em-bodiment, instructions or sub-operations of distinct operations may be implemented in an in-termittent and/or alternating manner.

The teachings of the disclosure provided herein can be applied to other systems, not necessarily the system described above. The elements and acts of the various embodiments described above can be combined to provide further embodiments. Any measurements or dimensions described or used herein are merely exemplary and not a limitation on the present invention. Other meas-urements or dimensions are within the scope of the invention.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the dis-closure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be con-strued to limit the disclosures to the specific embodiments disclosed in the specification unless the above Detailed Description of the Preferred Embodiments section explicitly defines such terms. Accordingly, the actual scope of the disclosure encompasses not only the disclosed em-bodiments, but also all equivalent ways of practicing or implementing the dis-closure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. §

112,¶6, other aspects may likewise be embodied as a means-plus-function claim, or in other forms, such as being embodied in a computer-readable medium. (Any claims intended to be treated under 35 U.S.C. § 112, ¶6 will include the words "means for"). Accordingly, the ap-plicant reserves the right to add additional claims after filing the application to pursue such ad-ditional claim forms for other aspects of the disclosure.

Accordingly, although exemplary embodiments of the invention have been shown and de-scribed, it is to be understood that all the terms used herein are descriptive rather than limiting, and that many changes, modifications, and substitutions may be made by one having ordinary skill in the art without departing from the spirit and scope of the invention.

What is claimed is:

1. A percussive massage device system comprising:
a hand-held percussive massage device configured to accept one of a plurality of types of massage attachments and having a plurality of handle portions that cooperate to at least partially define a handle opening, wherein each of the plurality of handle portions defines an axis that is co-planar to surround the handle opening and is configured to be independently grasped by a user to use the percussive massage device;
a command center configured to generate a unique activation code configured to be received by the percussive massage device, wherein the unique activation code is associated with the percussive massage device and is configured to activate the percussive massage device for a first predetermined period of time; and
an authentication device configured to be paired with the percussive massage device and provide the unique activation code to the percussive massage device;
wherein the percussive massage device is configured to:
receive the unique activation code from the authentication device,
activate the percussive massage device for the first predetermined period of time, and
receive a massage routine configured to be activated by the percussive massage device for a second predetermined period of time, wherein the massage routine includes at least one adjustable setting directed to: a location of the user's body part where the percussive massage device is to be applied, a selection of one of the plurality of handle portions of the percussive massage device, or one of a plurality of types of massage attachments for the percussive massage device,
wherein the massage routine is distinct from the unique activation code and is configured to be activated by the percussive massage device only after the unique activation code is received by the percussive massage device,
wherein the percussive massage device is configured to be in an inactive state unless activated by the unique activation code, and
wherein the percussive massage device is configured to return to the inactive state after the first predetermined period of time.

2. The percussive massage device system of claim 1 wherein the first predetermined period of time is one hour.

3. The percussive massage device system of claim 1 wherein the percussive massage device further comprises a wireless communication module.

4. The percussive massage device system of claim 1 wherein the first and second predetermined time periods of time are equal.

5. The percussive massage device system of claim 1 wherein the command center is further configured to maintain a list of percussive massage devices including the percussive massage device for which the unique activation code associated with the percussive massage device is generated.

6. The percussive massage device system of claim 1 further comprising a remote device including a user interface, wherein the user requests that the unique activation code be generated by the command center via the user interface.

7. The percussive massage device system of claim 6 wherein the remote device is a smart device on which an application is configured to request the unique activation code from the command center, receive the unique activation code from the command center, and provide the unique activation code to the percussive massage device.

8. The percussive massage device system of claim 6 wherein the remote device is the authentication device.

9. A method comprising the steps of:
generating a unique activation code, wherein the unique activation code is associated with a hand-held percussive massage device configured to accept one of a plurality of types of massage attachments and which has a plurality of handle portions that cooperate to at least partially define a handle opening, wherein each of the plurality of handle portions defines an axis that is co-planar to surround the handle opening and is configured to be independently grasped by a user to use the percussive massage device, and is configured to activate the percussive massage device for a first predetermined period of time;
providing the unique activation code to an authentication device configured to be paired with the percussive massage device;
pairing the authentication device with the percussive massage device;
providing the unique activation code to the percussive massage device from the authentication device;
activating the percussive massage device for the first predetermined period of time; and
receiving a massage routine configured to be activated by the percussive massage device for a second predetermined period of time, wherein the massage routine includes at least one adjustable setting directed to: a location of the user's body part where the percussive massage device is to be applied, a selection of one of the plurality of handle portions of the percussive massage device, or one of a plurality of types of massage attachments for the percussive massage device,
wherein the massage routine is distinct from the unique activation code and is configured to be activated by the percussive massage device only after the unique activation code is received by the percussive massage device,
wherein the percussive massage device is configured to be in an inactive state unless activated by the unique activation code, and
wherein the percussive massage device is configured to return to the inactive state after the first predetermined period of time.

10. The method of claim 9 wherein the first predetermined period of time is one hour.

11. The method of claim 9 wherein the first and second predetermined time periods are equal.

12. A method comprising the steps of:
receiving a wireless signal from a hand-held percussive massage device configured to accept one of a plurality of types of massage attachments and which has a plurality of handle portions that cooperate to at least partially define a handle opening, wherein each of the plurality of handle portions defines an axis that is co-planar to surround the handle opening and is configured to be independently grasped by a user to use the percussive massage device, at a remote device;

determining whether the percussive massage device is on a list of cleared devices from the wireless signal, wherein the percussive massage device is associated with a unique activation code that is configured to activate the percussive massage device for a first predetermined period of time;

deactivating the percussive massage device when the percussive massage device is not on the list of cleared devices; and receiving a massage routine configured to be activated by the percussive massage device for the first predetermined period of time when the percussive massage device is on the list of cleared devices, wherein the massage routine is distinct from the unique activation code and is configured to be activated by the percussive massage device only after the unique activation code is received by the remote device and is on the list of cleared devices, wherein the massage routine includes at least one adjustable setting directed to: a location of the user's body part where the percussive massage device is to be applied, a selection of one of the plurality of handle portions of the percussive massage device, or one of a plurality of types of massage attachments for the percussive massage device, wherein the percussive massage device is configured to be in an inactive state unless activated by the unique activation code, and wherein the percussive massage device is configured to return to the inactive state after the first predetermined period of time.

13. The method of claim 12 further comprising unlocking the percussive massage device when the percussive massage device receives an unlock command.

* * * * *